United States Patent
Boime et al.

[11] Patent Number: 6,103,501
[45] Date of Patent: Aug. 15, 2000

[54] SINGLE CHAIN GLYCOPROTEIN HORMONES COMPRISING TWO β AND ONE α SUBUNITS AND RECOMBINANT PRODUCTION THEREOF

[75] Inventors: Irving Boime; David Ben Menahem, both of St. Louis, Mo.

[73] Assignee: Washington University, St. Louis, Mo.

[21] Appl. No.: 08/971,439

[22] Filed: Nov. 17, 1997

[51] Int. Cl.$^7$ ............... C12N 15/16; C07K 14/59; C07K 19/00
[52] U.S. Cl. ............... 435/69.7; 435/325; 435/360; 435/365.1; 435/252.3; 435/320.1; 424/192.1; 424/198.1; 530/397; 530/398; 935/10; 536/23.4
[58] Field of Search ............... 435/69.7, 325, 435/360, 365.1, 252.3, 320.1; 424/192.1, 198.1; 530/395, 397, 398; 935/10; 536/23.4

[56] References Cited

U.S. PATENT DOCUMENTS

| | | | |
|---|---|---|---|
| 5,420,247 | 5/1995 | Gearing et al. | 530/350 |
| 5,705,484 | 1/1998 | Thomason | 514/2 |

FOREIGN PATENT DOCUMENTS

| | | |
|---|---|---|
| 0 163 406 | 12/1985 | European Pat. Off. . |
| 0 839 831 | 5/1998 | European Pat. Off. . |
| 01959 | 5/1985 | WIPO . |
| WO 90/09800 | 9/1990 | WIPO . |
| WO 91/16922 | 11/1991 | WIPO . |
| WO 95/22340 | 8/1995 | WIPO . |
| WO 96/05224 | 2/1996 | WIPO . |

OTHER PUBLICATIONS

Enhanced Stimulation of Follicle Maturation and Ovalatory Potential by Long Acting Follicle–Stimulating Hormone Agonists with Extended Carboxyl–Terminal Peptides, Philip S. LaPolt, et al., *Endocrinology* (1992) 131:2514–2520.

Design of a Long–Acting Follitropin Agonist by Fusing the C–Terminal Sequence of the Chorionic gonadotropin β subunit to the Follitropin β Subunit, Fuad A. Fares, et al., *Proc Natl Acad Sci USA* (1992)89:4304–4308.

Crystal Structure of Human Chorlonic Gonadotropin, A.J. Lapthorn, et al., *Nature* (1994) 369:455–461.

Structure of Human Chorionic Gonadotropin at 2.6 A Resolution From MAD Analysis of the Selecomethionyl Protein, Hao Wu, et al., *Structure* (1994) 2:545–558.

A Clasped Embrace, Dinshaw J. Patel, *Nature* (1994)369:438–439.

*Primary Examiner*—Lorraine Spector
*Attorney, Agent, or Firm*—Morrison & Foerster, LLP

[57] ABSTRACT

Single-chain agonists and/or antagonists of the glycoprotein hormones are disclosed. These proteins are of the formula $$\beta^1\text{-}(linker^1)_m\text{-}\alpha\text{-}(linker^2)_n\text{-}\beta^2 \qquad (1);$$

or $$\beta^1\text{-}(linker^1)_m\text{-}\beta^2\text{-}(linker^2)_n\text{-}\alpha \qquad (2);$$

or $$\alpha\text{-}(linker^1)_m\text{-}\beta^1\text{-}(linker^2)_n\text{-}\beta^2 \qquad (3)$$

wherein each of $\beta^1$ and $\beta^2$ has the amino acid sequence of the β subunit of a vertabrate glycoprotein hormone or a variant thereof; "α" designates the α subunit of a vertabrate glycoprotein hormone or a variant thereof; "linker" refers to a covalently linked moiety that spaces the $\beta^1$ and $\beta^2$ subunits at distances from the α subunit and from each other effective to retain said activity, and each of m and n is independently 0 or 1.

25 Claims, 2 Drawing Sheets

FIG. 1

HCG ng/100 μl or test compound μl/100 μl

FIG. 2

FSH ng/100 μl or test compound μl/100 μl

SINGLE CHAIN GLYCOPROTEIN HORMONES COMPRISING TWO β AND ONE α SUBUNITS AND RECOMBINANT PRODUCTION THEREOF

ACKNOWLEDGEMENT OF GOVERNMENT SUPPORT

This invention was made in part with government support under NIH Contract No. NO1-HD-9-2922, awarded by the National Institutes of Health. The government has certain rights in this invention.

TECHNICAL FIELD

The invention relates to the field of protein engineering, specifically to modified forms of certain glycoprotein hormones which occur normally as heterodimers. The invention concerns modified single-chain forms of chorionic gonadotropin (CG), thyroid stimulating hormone (TSH), luteinizing hormone (LH), and follicle stimulating hormone (FSH) that can provide two effects or functions, or can behave generally as agonists and/or antagonists of the native hormones.

BACKGROUND ART

In humans, four important glycoprotein hormone heterodimers (LH, FSH, TSH and CG) have identical α subunits and differing β subunits. Three of these hormones are present in virtually all other vertebrate species as well; CG has so far been found only in primates and in the placenta and urine of pregnant mares.

PCT application WO90/09800, published Sep. 7, 1990, and incorporated herein by reference, describes a number of modified forms of these hormones. One important modification is C-terminal extension of the β subunit by the carboxy terminal peptide (CTP) of human chorionic gonadotropin or a variant thereof. Other muteins of these hormones are also described. CTP is the sequence of amino acids extending from any one of positions 112–118 to position 145 of the β subunit of human chorionic gonadotropin. The PCT application describes variants of the CTP extension obtained by conservative amino acid substitutions such that the capacity of the CTP to alter the clearance characteristics is not destroyed. In addition, PCT application WO94/24148 published Oct. 27, 1994, incorporated herein by reference, describes modifying these hormones by extension or insertion of the CTP at locations other than the C-terminus and CTP fragments shorter than the sequence extending from positions 112–118 to 145.

The CTP-extended β subunit of FSH is also described in two papers by applicants herein: LaPolt, P. S. et al.; *Endocrinology* (1992) 131:2514–2520 and Fares, F. A. et al.; *Proc Natl Acad Sci USA* (1992) 89:4304–4308. Both of these papers are incorporated herein by reference.

The crystal structure of the heterodimeric form of human chorionic gonadotropin has now been published in more or less contemporaneous articles; one by Lapthorn, A. J. et al. *Nature* (1994) 369:455–461 and the other by Wu, H. et al. *Structure* (1994) 2:545–558. The results of these articles are summarized by Patel, D. J. *Nature* (1994) 369:438–439.

PCT application WO91/16922 published Nov. 14, 1991 describes a multiplicity of chimeric and otherwise modified forms of the heterodimeric glycoprotein hormones. In general, the disclosure is focused on chimeras of α subunits or β subunits involving portions of various α or β chains respectively. One construct simply listed in this application, and not otherwise described, fuses substantially all of the β chain of human chorionic gonadotropin to the α subunit preprotein, i.e., including the secretory signal sequence for this subunit.

Two additional published PCT applications describe single chain forms of these hormones wherein the α and β unit are covently linked to result in a fusion peptide of the general formula:

or wherein n is 0 or 1 and α and β represent the respective subunits of these hormones: Moyle, W. R., PCT application WO95/22340 published Aug. 24, 1995 and the application of the inventor herein, WO96/05224 published Feb. 22, 1996. The disclosure of these documents is also incorporated herein by reference.

Forms of the above-described single-chain glycoprotein hormones in which the number of cystine bridges has been depleted are disclosed in U.S. Ser. No. 08/933,693 filed Sep. 19, 1997, and incorporated herein by reference.

It has now been found possible to construct single-chain forms of the glycoprotein hormones which have enhanced agonist and/or antagonist activity and/or which are bifunctional by including two β subunits in a single-chain so that they share a common α subunit. These forms may contain various CTP extensions and insertions as well as variants of the native forms of the α and β subunits and of CTP as described in the documents set forth above.

DISCLOSURE OF THE INVENTION

The invention provides single-chain forms of the glycoprotein hormones that contain two β subunits that may be the same or different. The single-chain forms of the invention may either be glycosylated, partially glycosylated, or nonglycosylated and the α and β chains that occur in the native glycoprotein hormones or variants of them may optionally be linked through a linker moiety. Particularly preferred linker moieties include the carboxy terminal peptide (CTP) unit either as a complete unit or a variant including variants which represent only a portion thereof. The resulting single-chain hormones either retain or enhance the activity of the unmodified heterodimeric forms or are antagonists of this activity. If the two β subunits are different, they are bifunctional as agonists and/or antagonists.

Thus, in one aspect, the invention is directed to a glycosylated or nonglycosylated protein of the formula or or wherein each of $\beta^1$ and $\beta^2$ has the amino acid sequence of the β subunit of a vertabrate glycoprotein hormone or a variant of said amino acid sequence, wherein said variants are defined herein. "α" designates the α subunit of a vertabrate glycoprotein hormone or a variant thereof; "linker" refers to a covalently linked moiety that spaces the $\beta^1$ and $\beta^2$ subunits at appropriate distances from the α subunit and from each other. Each of m and n is independently 0 or 1.

In all of the foregoing cases, the single-chain form preserves conformation so that inclusion of the entire subunits in the single-chain forms is unnecessary. Thus, the invention includes compounds of formulas (1), (2) and (3) that comprise fragments of the α and/or β subunits wherein these forms retain the biological activity exhibited by the corresponding forms which contain the complete subunits.

In other aspects, the invention is directed to recombinant materials and methods to produce the proteins of the invention, to pharmaceutical compositions containing them; to antibodies specific for them; and to methods for their use.

MODES OF CARRYING OUT THE INVENTION

Four "glycoprotein" hormones in humans provide a family which includes human chorionic gonadotropin (hCG), follicle stimulating hormone (FSH), luteinizing hormone (LH), and thyroid stimulating hormone (TSH). As used herein, "glycoprotein hormones" refers to all the members of this family. All of these hormones are heterodimers comprised of α subunits which, for a given species, are identical in amino acid sequence among the group, and β subunits which differ according to the member of the family. Thus, normally these glycoprotein hormones occur as heterodimers composed of α and β subunits that are associated but not covalently linked. Most vertebrates produce FSH, TSH and LH; chorionic gonadotropin has been found only in primates, including humans, and in pregnant mares.

In animals, the α and β subunit of each hormone are encoded in different genes and are synthesized separately and then assembled into the noncovalent heterodimeric complex. In the compounds of the invention the β subunits are directly linked to an α subunit into a single-chain molecule which is essentially linear in primary structure. The three dimensional structure conferred by secondary and tertiary structural considerations and conformation is apparently sufficiently similar to the heterodimeric form to permit the functionality of the heterodimer represented by the β subunits to be exhibited. However, by suitable variation of the structures of the subunits, the compounds of the invention may have agonist or antagonist activity; for example, if the β subunits are different, the compounds may exhibit antagonist activity with respect to a receptor for one of the glycoprotein hormones but agonist activity for the receptor of another, or may have agonist or antagonist activity for both. The spectrum of the activities exhibited by the compounds of the invention will be dependent on the selection of the individual α and β subunits as well as the nature of the linker moieties and the orientation of the α and β subunits.

In the most preferred embodiment of the invention, the compounds of formulas (1), (2) or (3) are fusion proteins wherein the α and β subunits are linked head-to-tail either directly or through peptide linkers. Where only gene-encoded amino acids comprise the sequence, the compound can be synthesized recombinantly. However, it is unnecessary to restrict the compounds of the invention in this manner; the α and β subunits as well as the linkers may include amino acids that are not gene encoded. In addition, the linkers may be other than peptide-such as dicarboxylic acids or anydrides, diamines, or bifunctional linkers such as those sold by Pierce Chemical Co., Rockford, Ill. and the like. In addition, the subunits may be linked either directly or through a linker in a head-to-head or tail-to-tail configuration as well as a head-to-tail configuration as would be required in a fusion protein. Under these circumstances, for a head-to-head configuration, two amino groups may be linked through an anhydride or through any dicarboxylic acid derivative; two carboxyl groups can be linked through diamines or diols using standard activation techniques.

However, for convenience the most preferred form is a head-to-tail configuration wherein standard peptide linkages suffice and the compound can be prepared as a fusion protein recombinantly or using synthetic peptide techniques either in a single sequence of reactions or, preferably, ligating individual portions of the entire sequence.

Whatever the embodiment, the α and β subunits are joined to the remainder of the molecule at positions proximal to their N and C termini. It is preferred that these subunits be linked directly at their termini, however this linkage may simply be "proximal." In general, "proximal" indicates a position which is in within 10 amino acids, preferably within five amino acids, more preferably within two amino acids of the terminus, and most preferably at the terminus per se.

The Subunit Components

As used herein, the common α subunit, and FSH, LH, TSH, and CG β subunits as well as the heterodimeric forms have their conventional definitions and refer to the proteins having the amino acid sequences known in the art per se, or allelic variants thereof, regardless of the glycosylation pattern exhibited or other derivatization of the amino acid side chains.

"Native" forms of these peptides are those which have the amino acid sequences that have been isolated from the relevant vertebrate tissue, and have these known sequences per se, or those of their allelic variants.

"Variant" forms of these proteins and of CTP units (see below) are those which have deliberate alterations, including truncations, in amino acid sequences of the native protein produced by, for example, site-specific mutagenesis or by other recombinant manipulations, or which are prepared synthetically.

These alterations consist of 1–10, preferably 1–8, and more preferably 1–5 amino acid changes, including deletions, insertions, and substitutions, most preferably conservative amino acid substitutions. The resulting variants must retain an activity which affects the corresponding activity of the native hormone—i.e., either they must retain the biological activity of the native hormone so as to behave as agonists, or they must behave as antagonists, generally by virtue of being able to bind the receptors for the native hormones but lacking the ability to effect signal transduction.

"Conservative analog" means, in the conventional sense, an analog wherein the residue substituted is of the same general amino acid category as that for which substitution is made. Amino acids have been classified into such groups, as is understood in the art, by, for example, Dayhoff, M. et al, *Atlas of Protein Sequences and Structure* (1972) 5:89–99. In general, acidic amino acids fall into one group; basic amino acids into another; neutral hydrophilic amino acids into another; and so forth. More specific classifications are set forth in WO 96/05224 incorporated by reference above.

One set of preferred variants is that wherein the glycosylation sites of either the α or β subunits or both have been altered. Some useful variants of the hormone quartet described herein are set forth in U.S. Pat. No. 5,177,193 issued Jan. 5, 1993 and incorporated herein by reference. As shown therein, the glycosylation patterns can be altered by destroying the relevant sites or, in the alternative, by choice of host cell in which the protein is produced.

Alterations in amino acid sequence also include both insertions and deletions. Thus, truncated forms of the hormones are included among variants, e.g., mutants of the α subunit which are lacking some or all of the amino acids at positions 85–92 at the C-terminus. In addition, α subunits with 1–10 amino acids deleted from the N-terminus are included.

Variants also include those with noncritical regions altered or removed. Such deletions and alterations may comprise entire loops, so that sequences of considerably more than 10 amino acids may be deleted or changed. The resulting variants must, however, retain at least the receptor binding domains and/or the regions involved in signal transduction.

There is considerable literature on variants of the glycoprotein hormones and it is clear that a large number of possible variants which result both in agonist and antagonist activity can be prepared. Such variants are disclosed, for example, in Chen, F. et al. *Molec Endocrinol* (1992) 6:914–919; Yoo, J. et al. *J Biol Chem* (1993) 268:13034–13042; Yoo, J. et al. *J Biol Chem* (1991) 266:17741–17743; Puett, D. et al. *Glycoprotein Hormones*, Lusbader, J. W. et al. EDS, *Springer Verlag* New York (1994) 122–134; Kuetmann, H. T. et al. (ibid) pages 103–117; Erickson, L. D. et al. *Endocrinology* (1990) 126:2555–2560; and Bielinska, M. et al. *J Cell Biol* (1990) 111:330a (Abstract 1844).

Other variants include those wherein one or more cystine-bond is deleted, typically by substituting a neutral amino acid for one or both cysteines which participate in the link. Particularly preferred cystine bonds which may be deleted are those between positions 26 and 110 and between positions 23 and 72.

In addition, it has been demonstrated that the β subunits of the hormone quartet can be constructed in chimeric forms so as to provide biological functions of both components of the chimera, or, in general, hormones of altered biological function. Thus, chimeric molecules which exhibit both FSH and LH/CG activities can be constructed as described by Moyle, *Proc Natl Acad Sci* (1991) 88:760–764; Moyle, *Nature* (1994) 368:251–255. As disclosed in these papers, substituting amino acids 101–109 of FSH-β for the corresponding residues in the CG-β subunit yields an analog with both hCG and FSH activity.

As used herein "peptide" and "protein" are used interchangeably, since the length distinction between them is arbitrary.

As stated above, the "variants" employed as α and β subunits in forming compound of the invention with or without linking moieties may represent the complete amino acid sequences of the subunits or only portions thereof.

"Variants" also include α and/or β chains which contain a CTP (or a variant of CTP) inserted into a noncritical region.

"Noncritical" regions of the α and β subunits are those regions of the molecules not required for biological activity (including agonist and antagonist activity). In general, these regions are removed from binding sites, precursor cleavage sites, and catalytic regions. Regions critical for inducing proper folding, binding to receptors, catalytic activity and the like should be evaluated. It should be noted that some of the regions which are critical in the case of the dimer become noncritical in single chain forms since the conformational restriction imposed by the molecule may obviate the necessity for these regions. The ascertainment of noncritical regions is readily accomplished by deleting or modifying candidate regions and conducting an appropriate assay for the desired activity. Regions where modifications result in loss of activity are critical; regions wherein the alteration results in the same or similar activity (including antagonist activity) are considered noncritical.

It should again be emphasized, that by "biological activity" is meant activity which is either agonistic or antagonistic to that of the native hormones. Thus, certain regions are critical for behavior of a variant as an antagonist, even though the antagonist is unable to directly provide the physiological effect of the hormone.

For example, for the α subunit, positions 33–59 are thought to be necessary for signal transduction and the 20 amino acid stretch at the carboxy terminus is needed for signal transduction/receptor binding. Residues critical for assembly with the β subunit include at least residues 33–58, particularly 37–40.

Where the noncritical region is "proximal" to the N- or C-terminus, the insertion is at any location within 10 amino acids of the terminus, preferably within 5 amino acids, and most preferably at the terminus per se.

As used herein, the "CTP unit" refers to an amino acid sequence found at the carboxy terminus of human chorionic gonadotropin β subunit which extends from amino acid 112–118 to residue 145 at the C-terminus or to a portion thereof. Thus, each "complete" CTP unit contains 28–34 amino acids, depending on the N-terminus of the CTP.

By a "partial" CTP unit is meant an amino acid sequence which occurs between positions 112–118 to 145 inclusive, but which has at least one amino acid deleted from the shortest possible "complete" CTP unit (i.e. from positions 118–145). These "partial" sequences are included in the definition of "variants." The "partial" CTP units preferably contain at least one O-glycosylation site. Some nonglycosylated forms of the hormones are antagonists and are useful as such. The CTP unit contains four glycosylation sites at the serine residues at positions 121 (site 1); 127 (site 2); 132 (site 3); and 138 (site 4). The partial forms of CTP useful in agonists will contain one or more of these sites arranged in the order in which they appear in the native CTP sequence, although intervening sites may be omited.

In some cases, CTP units may be inserted or used as linkers in tandem. By "tandem" inserts or extensions is meant that the insert or extension contains at least two "CTP units." Each CTP unit may be complete or a fragment, and native or a variant. All of the CTP units in the tandem extension or insert may be identical, or they may be different from each other.

The "linker moiety" is a moiety that joins the α and β sequences without interfering with the activity that would otherwise be exhibited by the same α and β chains as members of a heterodimer, or which alters that activity to convert it from agonist to antagonist activity. The level of activity may change within a reasonable range, but the presence of the linker cannot be such so as to deprive the single-chain form of both substantial agonist and substantial antagonist activity. The single-chain form does not represent a propeptide but the mature protein and must exhibit activity pertinent to the hormonal activity of the heterodimer, the elements of which form its components.

Preferred Embodiments of the Bifunctional Hormones

The bifunctional hormones of the invention are most efficiently and economically produced using recombinant techniques. Therefore, fusion proteins comprising those forms of α and β chains, CTP units and other linker moieties which include only gene-encoded amino acids are preferred. It is possible, however, as set forth above, to construct at least portions of the single-chain hormones using synthetic peptide techniques or other organic synthesis techniques and therefore variants which contain nongene-encoded amino acids and nonpeptide based linkers are also within the scope of the invention.

In the most preferred embodiment, the C-terminus of the $\beta^1$ subunit is covalently linked, optionally through a linker, to the N-terminus of the mature α subunit which is in turn covalently Tinkered optionally through α linker to the $\beta^2$ subunit. The linkage can be a direct peptide linkage wherein the C-terminal amino acid of one subunit is directly linked through the peptide bond to the N-terminus of the other; however, in many instances it is preferable to include a linker moiety between the two termini. In many instances, the linker moiety will provide at least one β turn between the two chains. The presence of proline residues in the linker may therefore be advantageous.

(It should be understood that in discussing linkages between the termini of the subunits comprising the single chain forms, one or more termini may be altered by substitution and/or deletion as described above.)

In one particularly preferred set of embodiments, the linkage is head-to-tail and the linker moiety will include one or more CTP units and/or variants or truncated forms thereof. Preferred forms of the CTP units used in such linker moieties are described hereinbelow.

Further, the linker moiety may include a drug covalently, preferably releasably, bound to the linker moiety. Means for coupling the drug to the linker moiety and for providing for its release are conventional.

In addition to their occurrence in the linker moiety, CTP and its variants may also be included in any noncritical region of the subunits making up the single-chain hormone as described above.

While CTP units are preferred inclusions in the linker moiety, it is understood that the linker may be any suitable covalently bound material which provides the appropriate spatial relationship between the α and β subunits. Thus, for head-to-tail configurations the linker may generally be a bivalent moiety such as a peptide comprising an arbitrary number, but typically less than 100, more preferably less than 50 amino acids which has the proper hydrophilicity/hydrophobicity ratio to provide the appropriate spacing and conformation in solution or a nonpeptide linker which confers these characteristics. In general, the linker should be on balance hydrophilic so as to reside in the surrounding solution and out of the way of the interaction between the α and β subunits or the two β subunits. It is preferable that the linker include β turns typically provided by proline residues in peptide linkers, or comprise serine and/or glycine residues. Any suitable polymer, including peptide linkers, with the above-described correct characteristics may be used.

Particularly preferred embodiments of the bifunctional hormones of the invention include in head-to-tail configuration:

βFSH-α-βFSH; α-βFSH-βLH; βFSH-α-βLH;
βLH-α-βLH; α-βLH-βFSH; βLH-α-βFSH;
βTSH-α-βTSH; βTSH-βFSH-α; βTSH-α-βFSH;
βCG-α-βCG; α-βCG-βFSH; α-βCG-βTSH; βCG-βFSH-α; βCG-α-βTSH;
βFSH-βCTP-αβFSH; α-βFSH-CTP-βLH; βFSH-CTP-α-βLH;
βLH-CTP-αβLH; α-βLH-CTP-βFSH; βLH-α-CTP-βFSH;
βLH(δ115–123)-α-βFSH; βLH(δ115–123)-CTP-α-βFSH;
βCG-CTP-α CTP-βFSH-CTP-CTP;
βTSH-CTP-CTP-αβFSH-CTP-CTP;
βFSH-CTP-CTP-α-βLH; βLH-CTP-CTP-βLH-α;
βCG-CTP-CTP-α-βTSH; βCG-CTP-CTP-βLH-α;
βFSH-CTP-βLH(δ115–123)-CTP-α;

and the like. Also particularly preferred are the human forms of the subunits. In the above constructions, "CTP" refers to CTP or its variants including truncations as described in No. 96/05224.

While for human use, the human forms of the α and β subunits are desirable, it should be noted that the corresponding forms in other vertebrates are useful in veterinary contexts. Thus, the FSH, TSH and LH subunits characteristic of bovine, ovine, equine, porcine, feline, canine, and other species are appropriate to indications affecting these species per se.

Suitable drugs that may be included in the linker moiety include peptides or proteins such as insulin-like growth factors; epidermal growth factors; acidic and basic fibroblast growth factors; platelet-derived growth factors; the various colony stimulating factors, such as granulocyte CSF, macrophage-CSF, and the like; as well as the various cytokines such as IL-2, IL-3 and the plethora of additional interleukin proteins; the various interferons; tumor necrosis factor; and the like. Suitable cleavage sites for the release of these drugs may be included, such as target sequences for proteases whose target sites are not present in the α and β subunits. Peptide- or protein-based drugs have the advantage that the entire construct can readily be produced by recombinant expression of a single gene. Also, small molecule drugs such as antibiotics, antiinflammatories, toxins, and the like can be used.

In general, the drugs included within the linker moiety will be those desired to act in the proximity of the receptors to which the hormones ordinarily bind. Suitable provision for release of the drug from inclusion within the linker will be provided, for example, by also including sites for enzyme-catalyzed lysis as further described under the section headed Preparation Methods hereinbelow.

Other Modifications

The single-chain proteins of the invention may be further conjugated or derivatized in ways generally understood to derivatize amino acid sequences, such as phosphorylation, glycosylation, deglycosylation of ordinarily glycosylated forms, acylation, modification of the amino acid side chains (e.g., conversion of proline to hydroxyproline) and similar modifications analogous to those posttranslational events which have been found to occur generally.

The glycosylation status of the hormones of the invention is particularly important. The hormones may be prepared in nonglycosylated form either by producing them in procaryotic hosts or by mutating the glycosylation sites normally present in the subunits and/or any CTP units that may be present. Both nonglycosylated versions and partially glycosylated versions of the hormones can be prepared by manipulating the glycosylation sites. Normally, glycosylated versions are, of course, also included within the scope of the invention.

As is generally known in the art, the single-chain proteins of the invention may also be coupled to labels, carriers, solid supports, and the like, depending on the desired application. The labeled forms may be used to track their metabolic fate;

suitable labels for this purpose include, especially, radioisotope labels such as iodine 131, technetium 99, indium 111, and the like. The labels may also be used to mediate detection of the single-chain proteins in assay systems; in this instance, radioisotopes may also be used as well as enzyme labels, fluorescent labels, chromogenic labels, and the like. The use of such labels permits localization of the relevant receptors since they can be used as targeting agents for such receptors.

The proteins of the invention may also be coupled to carriers to enhance their immunogenicity in the preparation of antibodies specifically immunoreactive with these new modified forms. Suitable carriers for this purpose include keyhole limpet hemocyanin (KLH), bovine serum albumin (BSA) and diphtheria toxoid, and the like. Standard coupling techniques for linking the modified peptides of the invention to carriers, including the use of bifunctional linkers, can be employed.

Similar linking techniques, along with others, may be employed to couple the proteins of the invention to solid supports. When coupled, these proteins can then be used as affinity reagents for the separation of desired components with which specific reaction is exhibited. Thus, they are useful in the purification and isolation of the receptors with which the appropriate β subunit interacts.

Preparation Methods

Methods to construct the proteins of the invention are well known in the art. As set forth above, if only gene encoded amino acids are included, and the single-chain is in a head-to-tail configuration, the most practical approach at present is to synthesize these materials recombinantly by expression of the DNA encoding the desired protein. DNA containing the nucleotide sequence encoding the single-chain forms, including variants, can be prepared from native sequences, or synthesized de novo or using combinations of these techniques. Techniques for site-directed mutagenesis, ligation of additional sequences, amplification such as by PCR, and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available compatible with a wide variety of hosts, including procaryotic hosts such as E. coli or B. subtilis and eucaryotic hosts such as yeast, other fungi such as Aspergillus and Neurospora, plant cells, insect cells, mammalian cells such as CHO cells, avian cells, and the like.

The choice of host is particularly pertinent to posttranslational events, most particularly including glycosylation. The location of glycosylation is mostly controlled by the nature of the glycosylation sites within the molecule; however, the nature of the sugars occupying this site is largely controlled by the nature of the host. Accordingly, a fine-tuning of the properties of the hormones of the invention can be achieved by proper choice of host.

A particularly preferred form of gene for the α, subunit portion, whether the α subunit is modified or unmodified, is the "minigene" construction. As used herein, the α subunit "minigene" refers to the gene construction disclosed in Matzuk, M. M., et al., *Mol Endocrinol* (1988) 2:95–100, in the description of the construction of $pM^2/CG$ α or $pM^2/I$.

For recombinant production, modified host cells using expression systems are used and cultured to produce the desired protein. These terms are used herein as follows:

A "modified" recombinant host cell, i.e., a cell "modified to contain" the recombinant expression systems of the invention, refers to a host cell which has been altered to contain this expression system by any convenient manner of introducing it, including transfection, viral infection, and so forth. "Modified cells" refers to cells containing this expression system whether the system is integrated into the chromosome or is extrachromosomal. The "modified cells" may either be stable with respect to inclusion of the expression system or the encoding sequence may be transiently expressed. In short, recombinant host cells "modified" with the expression system of the invention refers to cells which include this expression system as a result of their manipulation to include it, when they natively do not, regardless of the manner of effecting this incorporation.

"Expression system" refers to a DNA molecule which includes a coding nucleotide sequence to be expressed and those accompanying control sequences necessary to effect the expression of the coding sequence. Typically, these controls include a promoter, termination regulating sequences, and, in some cases, an operator or other mechanism to regulate expression. The control sequences are those which are designed to be functional in a particular target recombinant host cell and therefore the host cell must be chosen so as to be compatible with the control sequences in the constructed expression system.

If secretion of the protein produced is desired, additional nucleotide sequences encoding a signal peptide are also included so as to produce the signal peptide operably linked to the desired single-chain hormone to produce the preprotein. Upon secretion, the signal peptide is cleaved to release the mature single-chain hormone.

As used herein "cells," "cell cultures," and "cell lines" are used interchangeably without particular attention to nuances of meaning. Where the distinction between them is important, it will be clear from the context. Where any can be meant, all are intended to be included.

The protein produced may be recovered from the lysate of the cells if produced intracellularly, or from the medium if secreted. Techniques for recovering recombinant proteins from cell cultures are well understood in the art, and these proteins can be purified using known techniques such as chromatography, gel electrophoresis, selective precipitation, and the like.

All or a portion of the hormones of the invention may be synthesized directly using peptide synthesis techniques known in the art. Synthesized portions may be ligated, and release sites for any drug contained in the linker moiety introduced by standard chemical means. For those embodiments which contain amino acids which are not encoded by the gene and those embodiments wherein the head-to-head or tail-to-tail configuration is employed, of course, the synthesis must be at least partly at the protein level. Head-to-head junctions at the natural N-termini or at positions proximal to the natural N-termini may be effected through linkers which contain functional groups reactive with amino groups, such as dicarboxylic acid derivatives. Tail-to-tail configurations at the C-termini or positions proximal to the C-termini may be effected through linkers which are diamines, diols, or combinations thereof.

Antibodies

The proteins of the invention may be used to generate antibodies specifically immunoreactive with these new compounds. These antibodies are useful in a variety of diagnostic and therapeutic applications.

The antibodies are generally prepared using standard immunization protocols in mammals such as rabbits, mice, sheep or rats, and the antibodies are titered as polyclonal antisera to assure adequate immunization. The polyclonal antisera can then be harvested as such for use in, for example, immunoassays. Antibody-secreting cells from the host, such as spleen cells, or peripheral blood leukocytes, may be immortalized using known techniques and screened for production of monoclonal antibodies immunospecific with the proteins of the invention. "Antibodies" include any fragment which retains the required immunospecificity, such as $F_{ab}$, $F_{ab'}$, $F_{(ab')2}$, $F_v$ and so forth. Thus, the antibodies may also be prepared using recombinant techniques, typically by isolating nucleotide sequences encoding at least the variable regions of monoclonal antibodies with the appropriate specificity and constructing appropriate expression systems. This approach permits any desired modification such as production of $F_v$ forms, chimeric forms, "humanized" forms and the like.

By "immunospecific for the proteins of the invention" is meant antibodies which specifically bind the referent compound of the invention, but not the heterodimers or any of the included subunits per se or any single-chain forms which include only a single β subunit within the general parameters considered to determine affinity or nonaffinity. It is understood that specificity is a relative term, and an arbitrary limit could be chosen, such as a difference in specific binding of 100-fold or greater. Thus, an immunospecific antibody included within the invention is at least 100 times more reactive with the single-chain protein than with the corresponding heterodimers, prior art single-chain forms or separate subunits. Such antibodies can be obtained, for example, by screening for those that bind the invention compounds and discarding those that also bind the heterodimers, subunits or prior art single-chain forms set forth in WO95/22340 and WO96/05224.

Formulation and Methods of Use

The proteins of the invention are formulated and administered using methods comparable to those known for the heterodimers corresponding to them. Thus, formulation and administration methods will vary according to the particular hormone or hormone combination used. However, the dosage level and frequency of administration may be altered as compared to the heterodimer, especially if CTP units are present in view of the extended biological half life due to its presence.

Formulations for proteins of the invention are those typical of protein or peptide drugs such as found in *Remington's Pharmaceutical Sciences*, latest edition, Mack Publishing Company, Easton, Pa. Generally, proteins are administered by injection, typically intravenous, intramuscular, subcutaneous, or intraperitoneal injection, or using formulations for transmucosal or transdermal delivery. These formulations generally include a detergent or penetrant such as bile salts, fusidic acids, and the like. These formulations can be administered as aerosols or suppositories or, in the case of transdermal administration, in the form of skin patches. Oral administration is also possible provided the formulation protects the peptides of the invention from degradation in the digestive system.

Optimization of dosage regimen and formulation is conducted as a routine matter and as generally performed in the art. These formulations can also be modified to include those suitable for veterinary use.

The compounds of the invention may be used in many ways, most evidently as substitutes for the heterodimeric forms of the hormones. Thus, like the heterodimers, the agonist forms of the single-chain hormones of the invention can be used in treatment of infertility, as aids in in vitro fertilization techniques, and other therapeutic methods associated with the native hormones. These techniques are applicable to humans as well as to other animals. The choice of the single-chain protein in terms of its species derivation will, of course, depend on the subject to which the method is applied. It will be realized that the dual functionality which is conferred on those compounds which contain two different β subunits confers opportunities for therapies that have previously been unavailable.

The invention compounds are also useful as reagents in a manner similar to that employed with respect to the heterodimers.

In addition, the compounds of the invention may be used as diagnostic tools to detect the presence or absence of antibodies that bind to the native proteins to the extent such antibodies bind to the relevant portions of these single chain compounds in biological samples. They are also useful as control reagents in assay kits for assessing the levels of these hormones in various samples. Protocols for assessing levels of the hormones themselves or of antibodies raised against them are standard immunoassay protocols commonly known in the art. Various competitive and direct assay methods can be used involving a variety of labeling techniques including radio-isotope labeling, fluorescence labeling, enzyme labeling and the like.

The compounds of the invention are also useful in detecting and purifying receptors to which the native hormones bind. Thus, the compounds of the invention may be coupled to solid supports and used in affinity chromatographic preparation of receptors or antihormone antibodies. The resulting receptors are themselves useful in assessing hormone activity for candidate drugs in screening tests for therapeutic and reagent candidates. Of course, account must be taken of the dual specificity of the β subunits in any of these compounds where the β subunits are different. However, where the two β subunits are identical, they offer a powerful affinity purification tool for the relevant receptor.

Finally, the antibodies uniquely reactive with the compounds of the invention can be used as purification tools for isolation of these materials in their subsequent preparations. They can also be used to monitor levels of these compounds administered as drugs.

The following examples are intended to illustrate but not to limit the invention.

EXAMPLE 1

Preparation of CGβ-α-CTP-FSHβ

A nucleotide sequence encoding the title compound was prepared using the available nucleotide sequences for the relevant portions of the subunits. The CGβ region encodes the 145 amino acids of human CGβ; the α subunit-encoding nucleotide sequence encodes the 92 amino acids of human α as the minigene; the CTP-encoding sequence encodes 28 amino acids representing positions 118–145 of human chorionic gonadotropin; and the FSHβ encoding region encodes the 111 amino acids of the human FSHβ subunit.

An amplified fragment containing CGβ exon 3, the α minigene, CTP and βFSH was inserted into the SalI site of pM$^2$HA-CGβexon1,2 an expression vector which is derived from pM$^2$ and containing CGβ exons 1 and 2 in the manner described by Sachais, β *Biol Chem* (1993) 268:2319. pM$^2$ containing CGβ exons 1 and 2 is described in Matzuk, M. M. et al. *Proc Natl Acad USA* (1987) 84:6354–6358 and Matzuk, M. M. et al. *J Cell Biol* (1988) 106:1049–1059. First, a fragment containing the α minigene downstream of CGβ exon 3 was inserted into this vector to obtain pM$^2$-

HACGβα. pM²-HACGβα was then cleaved with ScaI and ligated with ScaI restricted pBIIKS(+)α-CTP-FSH. The resulting expression vector pM²-HACGβ-α-CTP-FSH produces the title compound when inserted into a suitable host.

EXAMPLE 2

Production and Activity of the CGβ-α-CTP-FSHβ

The expression vector constructed in Example 1 was transfected into Chinese hamster ovary (CHO) cells and production of the protein was assessed by immunoprecipitation of radiolabeled protein on SDS gels.

The culture medium was collected, concentrated and tested for binding to the human LH receptor (expected to bind the βCG- α portion).

For this assay, the LH receptor was prepared by inserting the cDNA encoding the entire human LH receptor into the expression vector pCMX (Oikawa, J. X-C et al. *Mol Endocrinol* (1991) 5:759–768). Exponentially growing 293 cells were transfected with this vector using the method of Chen, C. et al. *Mol Cell Biol* (1987) 7:2745–2752, resulting in expression of the LH receptor at the surface.

Figure 1:
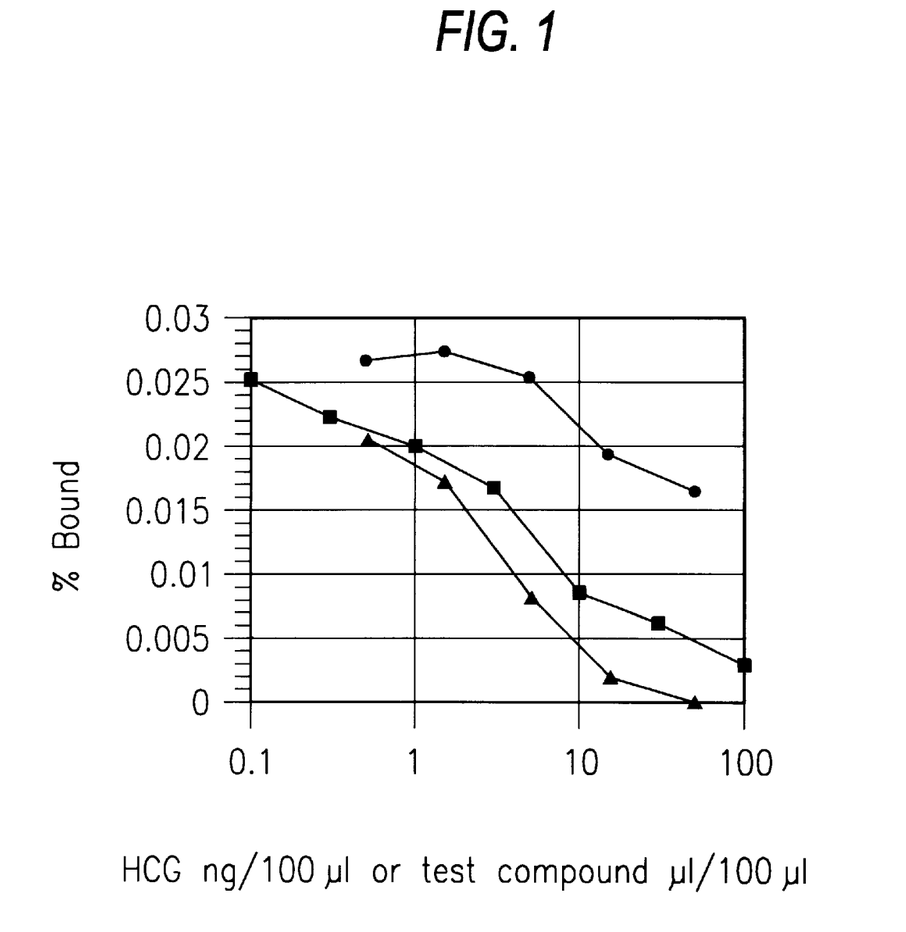
FIG. 1 shows the binding of the compound CGβ-α-CTP-FSHβ to the LH receptor in competition with hCG.

In the assay, the cells expressing human LH receptor (2×10⁵/tube) were incubated with 1 ng of labeled hCG in competition with increasing concentrations of unlabeled hCG or increasing amounts of the sample to be tested at 22° C. for 18 hours. The decrease in label in the presence of sample measures the binding ability in the sample. In this assay, with respect to the human LH receptor in 293 cells, the heterodimeric hCG had an activity typical of wild-type as previously determined and the CGβ-α-CTP-FSHβ-containing medium also showed activity. These results are shown in FIG. 1. As shown, both heterodimeric (solid squares) hCG and the bifunctional single-chain protein of the invention (solid circles) competed successfully with labled hCG for LH receptor. The bifunctional compound is less potent due to the modification of the α subunit carboxy terminus.

Also shown in FIG. 1 are the results of the assay wherein varying amounts of a culture supernatant derived from cells modified to contain two expression systems was tested. One expression system produced a single chain FSHβ-α; the other produced the β subunit of hCG. The resulting noncovalently associated single-chain FSHα-β/CGβ complex (solid triangles) also successfully competed for binding.

Figure 2:
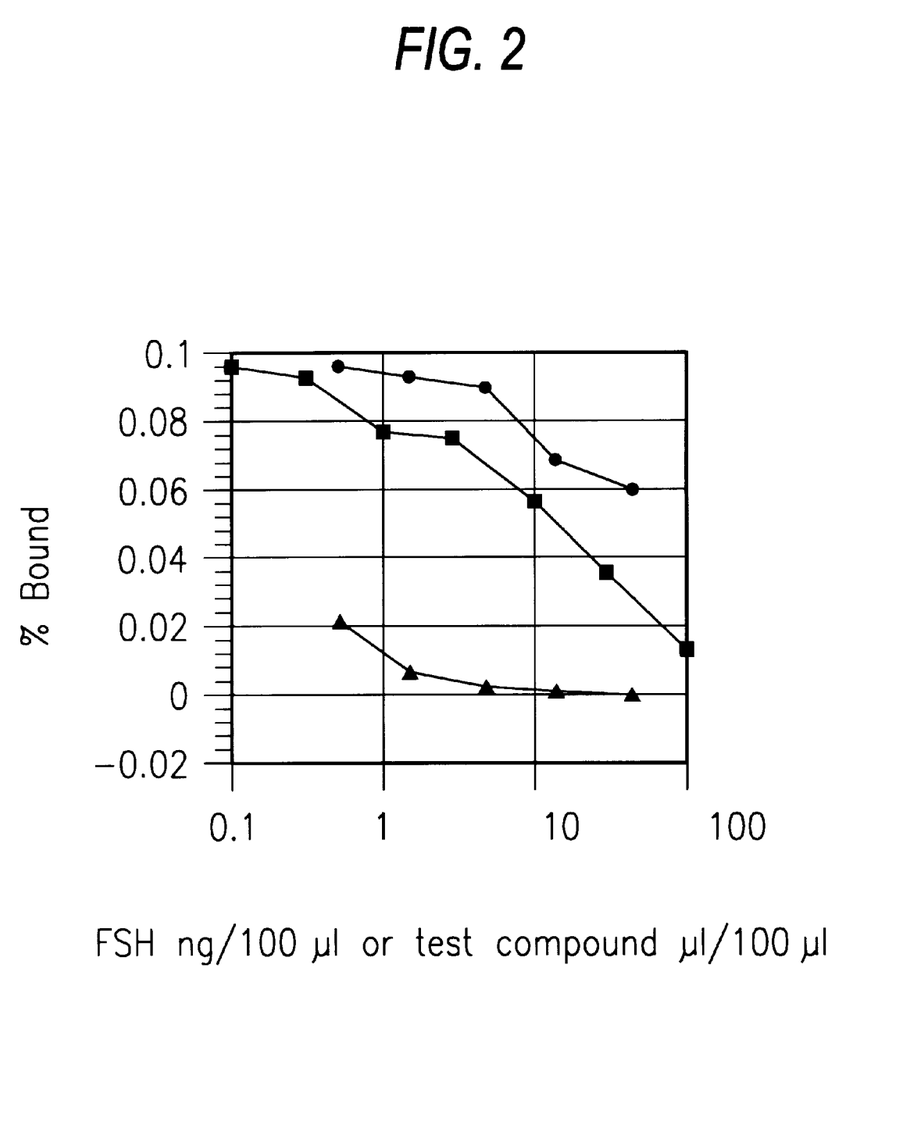
FIG. 2 shows the binding of the compound shown in FIG. 1 to the FSH receptor in competition with FSH.

In a similar manner, the supernatant from the culture medium containing CGβ-α-CTP-FSHβ was tested for binding to the receptor for FSH, expressed in 293 cells. The assay was conducted in the manner described above, except that cells expressing the human FSH receptor were substituted for those expressing human LH receptor and labeled FSH was used as the competitor. The results of this assay are shown in FIG. 2.

As shown, the single-chain title compound (solid circles) competed successfully with FSH (solid squares) for binding. In an unrelated experiment, also shown in FIG. 2, the mixture of a different type of complex—i.e., single-chain FSHβ-α noncovalently associated with CGβ—which is mixed with uncomplexed excess single-chain FSHβ-α (solid triangles), was an excellent competitor.

EXAMPLE 3

Construction of Additional Expression Vectors

In a manner similar to that set forth in Example 1, expression vectors for the production of single-stranded bifunctional FSHβ-CTP-α-CG β; α- FSHβ-CTP-CG β, CG β- βFSH-CTP-α, and βLH-CTP- βFSH-CTP-α are prepared and transfected into CHO cells. The culture supernatants are cultured and tested as described above with respect both to the LH and FSH receptors. These compounds, too, show ability to bind bothreceptors.

We claim:

1. A glycosylated or nonglycosylated protein having agonist and/or antagonist activity of the formula (1);

or (2);

or (3)

wherein each of $\beta^1$ and $\beta^1$ has the amino acid sequence of the β subunit of a vertebrate glycoprotein hormone which is selected from the group consisting of thyroid stimulating hormone (TSH), follicle stimulating hormone (FSH), leutinizing hormone (LH) and chorionic gonadotrophin (CG) or a variant thereof which variant binds to the receptor for said β-subunit;

"α" designates the α subunit of a vertebrate glycoprotein hormone TSH, FSH, LH or CG or a variant thereof;

"linker" refers to a covalently linked moiety that spaces the $\beta^1$ and $\beta^2$ subunits at distances from the α subunit and from each other effective to retain said activity, and each of m and n is independently 0 or 1;

wherein said agonist and/or antagonist activity is with respect to the receptor for which at least one of said β subunits is a ligand.

2. The protein of claim 1 wherein said m and n are 1.

3. The protein of claim 1 wherein $\beta^1$ is the β subunit of FSH, LH or TSH extended at a position proximal to its C-terminus by a complete or partial CTP unit or variant thereof wherein said partial CTP unit or variant thereof comprises at least one O-glycosylation site of a native CTP unit.

4. The protein of claim 1 wherein one or more of the α and β subunits are modified by the insertion of a CTP unit or variant thereof into a noncritical region thereof and/or wherein said linker moiety includes a CTP unit or variant thereof.

5. The protein of claim 1 wherein said variants contain 1–5 conservative amino acid substitutions as referred to the native forms or lack 1–10 amino acids at the N or C terminus of said sequences or both contain substitutions and lack 1–10 amino acids at the N or C terminus and wherein said variants in the context of said protein retain the ability to bind receptor for which at least one of said β-subunits is a ligand.

6. A pharmaceutical composition which comprises the protein of claim 1 in admixture with a pharmaceutically acceptable excipient.

7. The protein of claim 1 coupled to a solid support.

8. A DNA or RNA molecule which comprises a nucleotide sequence encoding the protein of claim 1.

9. An expression system for production of an agonist and/or antagonist of a glycoprotein hormone which expression system comprises a first nucleotide sequence encoding the protein of claim 1 operably linked to control sequences capable of effecting the expression of said first nucleotide sequence.

10. The expression system of claim 9 which further contains a second nucleotide sequence encoding a signal peptide operably linked to the protein encoded by said first nucleotide sequence.

11. A host cell modified to contain the expression system of claim 10.

12. A method to produce a single-chain protein which is an agonist and/or antagonist of a glycoprotein hormone which method comprises culturing the cells of claim 1 under conditions wherein said protein is produced; and recovering said protein from the culture.

13. A host cell modified to contain the expression system of claim 9.

14. A method to produce a single-chain protein which is an agonist and/or antagonist of a glycoprotein hormone which method comprises culturing the cells of claim 13 under conditions wherein said protein is produced; and recovering said protein from the culture.

15. The protein of claim 1 which is of the formula $\beta^1\text{-(linker}^1)_m\text{-}\alpha\text{-(linker}^2)_n\text{-}\beta^2$ (1).

16. The protein of claim 15 wherein said $\beta$ and $\alpha$ subunits are linked in head-to-tail configuration.

17. The protein of claim 16 wherein one of m and n is 0 and the other is 1 and wherein the linker is CTP.

18. The protein of claim 17 wherein m is 0, n is 1 and linker$^2$ is CTP.

19. The protein of claim 18 which is CG$\beta$-$\alpha$-CTP-FSH$\beta$.

20. The protein of claim 1 which is of the formula $\beta^1\text{-(linker}^1)_m\text{-}\beta^2\text{-(linker}^2)_n\text{-}\alpha$(2).

21. The protein of claim 20 wherein said $\beta$ and $\alpha$ subunits are linked in head-to-tail configuration.

22. The protein of claim 21 wherein one of m and n is 0 and the other is 1 and wherein the linker is CTP.

23. The protein of claim 1 which is of the formula $\alpha\text{-(linker}^1)_m\text{-}\beta^1\text{-(linker}^2)_n\text{-}\beta^2$(3).

24. The protein of claim 23 wherein said $\beta$ and $\alpha$ subunits are linked in head-to-tail configuration.

25. The protein of claim 24 wherein one of m and n is 0 and the other is 1 and wherein the linker is CTP.

* * * * *

UNITED STATES PATENT AND TRADEMARK OFFICE

CERTIFICATE OF CORRECTION

PATENT NO. : 6,103,501

DATED : Aug. 15, 2000

INVENTOR(S) : Irving Boime et al.

It is certified that error appears in the above-identified patent and that said Letters Patent is hereby corrected as shown below:

In Claim 1, line 19, change "$\beta^1$", 2nd occurrence, to --$\beta^2$--.

In Claim 12, line 9, change "claim 1" to --claim 11--.

Signed and Sealed this

First Day of May, 2001

Attest:

NICHOLAS P. GODICI

*Attesting Officer*   *Acting Director of the United States Patent and Trademark Office*